(12) United States Patent
Koerner et al.

(10) Patent No.: US 7,584,903 B2
(45) Date of Patent: Sep. 8, 2009

(54) MICRODOSING DEVICE

(75) Inventors: Joachim Koerner, Uhldingen (DE); Michael Helmlinger, Radolfzell (DE); Holger Schuerle, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 565 days.

(21) Appl. No.: 11/051,964

(22) Filed: Feb. 4, 2005

(65) Prior Publication Data
US 2005/0207917 A1  Sep. 22, 2005

(30) Foreign Application Priority Data
Feb. 5, 2004  (DE) .................. 10 2004 006 452

(51) Int. Cl.
- *B05B 1/08* (2006.01)
- *B05B 17/04* (2006.01)
- *B05B 9/00* (2006.01)
- *B05C 1/00* (2006.01)
- *B05B 1/30* (2006.01)
- *A61M 11/00* (2006.01)
- *B05B 17/06* (2006.01)
- *B41J 2/045* (2006.01)

(52) U.S. Cl. .................. 239/102.2; 239/102.1; 239/4; 239/575; 239/127; 239/135; 128/200.14; 128/200.16; 347/68; 347/70

(58) Field of Classification Search .............. 239/102.1, 239/102.2, 4, 575, 127, 135, 1; 128/200.14, 128/200.16; 347/68, 70
See application file for complete search history.

(56) References Cited

U.S. PATENT DOCUMENTS

| | | | | |
|---|---|---|---|---|
| 3,790,079 A | * | 2/1974 | Berglund et al. .............. 239/3 |
| 4,420,943 A | * | 12/1983 | Clawson ........................ 62/81 |
| 5,487,378 A | | 1/1996 | Robertson et al. |
| 5,660,167 A | * | 8/1997 | Ryder .................. 128/200.21 |
| 5,666,946 A | * | 9/1997 | Langenback ........... 128/200.16 |
| 5,692,680 A | * | 12/1997 | Harwath et al. ............. 239/127 |
| 6,036,105 A | * | 3/2000 | Sanada et al. ............... 239/104 |
| 6,079,633 A | * | 6/2000 | Inoue et al. ..................... 239/1 |
| 6,129,702 A | * | 10/2000 | Woias et al. .................. 604/65 |

(Continued)

FOREIGN PATENT DOCUMENTS

DE  10102152 C1  6/2002

(Continued)

OTHER PUBLICATIONS

Observations Under Article 115 EPC dated Jul. 28, 2006 (2 pages).

(Continued)

*Primary Examiner*—Len Tran
*Assistant Examiner*—Steven Cernoch
(74) *Attorney, Agent, or Firm*—Flynn, Thiel, Boutel & Tanis, P.C.

(57) ABSTRACT

A microdosing device includes a dosing chamber which at least temporarily receives a quantity of liquid, and to which at least one dispensing opening is assigned. A vibration unit is operatively connected to at least one boundary surface of the dosing chamber in order to cause this boundary surface to oscillate for the purpose of a dispensing operation.

At least two admission channels spaced apart from one another are provided on the dosing chamber.

8 Claims, 1 Drawing Sheet

U.S. PATENT DOCUMENTS

| | | | |
|---|---|---|---|
| 6,196,219 B1 * | 3/2001 | Hess et al. | 128/200.21 |
| 6,267,820 B1 * | 7/2001 | Chen et al. | 118/726 |
| 6,722,582 B2 * | 4/2004 | Hess et al. | 239/102.2 |
| 2002/0092519 A1 * | 7/2002 | Davis | 128/200.14 |
| 2003/0081072 A1 * | 5/2003 | Trueba | 347/63 |
| 2003/0102384 A1 * | 6/2003 | Walter et al. | 239/102.2 |
| 2003/0186474 A1 * | 10/2003 | Haluzak et al. | 438/21 |
| 2003/0192959 A1 | 10/2003 | Hess et al. | |
| 2004/0074557 A1 | 4/2004 | Zengerle et al. | |

FOREIGN PATENT DOCUMENTS

| | | |
|---|---|---|
| EP | 0923957 A1 | 6/1999 |
| EP | 1 273 355 A1 | 1/2003 |
| EP | 1273355 A1 * | 1/2003 |
| EP | 1287905 A1 * | 3/2003 |

OTHER PUBLICATIONS

European Patent Office Search Report dated May 30, 2005 (3 pages).

German Office Action dated Aug. 6, 2004 (3 pages).

* cited by examiner

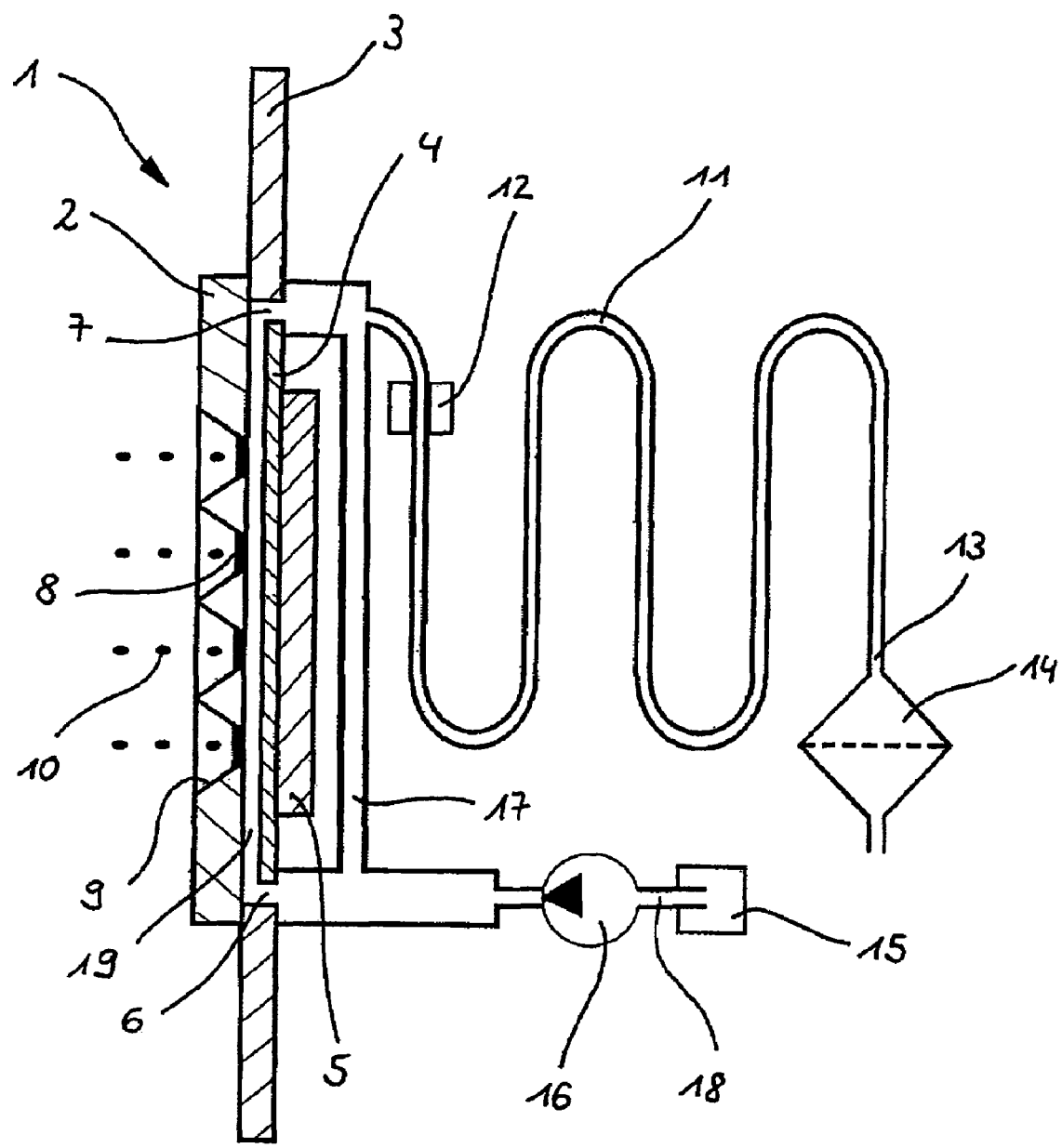

MICRODOSING DEVICE

FIELD OF THE INVENTION

The invention relates to a microdosing device with a dosing chamber which at least temporarily receives a quantity of liquid and to which at least one dispensing opening is assigned, and with a vibration unit which is operatively connected to at least one boundary surface of the dosing chamber in order to cause this boundary surface to oscillate for the purpose of a dispensing operation.

BACKGROUND OF THE INVENTION

Microdosing devices for dispensing small and very small droplets are known from cosmetic or pharmaceutical medium dispensers, such as inhaler devices for liquid medical substances. These have a dosing chamber which can be filled from a medium reservoir with a quantity of liquid and which has at least one dispensing opening through which the liquid can escape after a flow resistance has been overcome. The flow resistance is determined in particular by the size, geometry and material of the dispensing opening and by a surface tension and a viscosity of the liquid. In order to overcome this flow resistance, a vibration unit is provided on at least one boundary surface of the dosing chamber and is able to cause the dosing chamber to oscillate. As a result of the oscillations, pressure waves develop in the liquid, and these pressure waves at least temporarily overcome the flow resistance of the dispensing opening. In this way, the liquid can be expelled through the dispensing opening and into an environment.

SUMMARY OF THE INVENTION

The object of the invention is to make available a microdosing device of the type mentioned at the outset which ensures that the dosing chamber is reliably supplied with the liquid to be dispensed.

This object is achieved by the fact that at least two admission channels spaced apart from one another are provided on the dosing chamber. Admission channels form a communicating link between the dosing chamber and medium-conveying components situated upstream, such as a filling means designed in particular as medium pump, which can also be designed as a capillary tube or as a pressurized container system with rise pipe and can establish a connection to a medium reservoir. The admission channels thus allow the liquid to flow from the medium reservoir into the dosing chamber. In the case where there is a single admission channel on the dosing chamber, as is known from the prior art, it is often not possible to guarantee uniform supply of the entire dosing chamber with liquid during one dispensing operation. With known microdosing devices, the demands imposed in many application cases are at best satisfied.

For increased demands on dosing accuracy and/or on dispersion of dispensed droplets of the liquid, known microdosing devices are suitable only to a qualified extent. By contrast, the dosing chamber according to the invention, on which at least two admission channels spaced apart from one another are provided, permits an increase in dosing accuracy and improved dispersion of the droplets and at the same time also a reduction in the production costs of the microdosing device. The production costs for a microdosing device are affected in particular by the size of delivery means used to convey the liquid from the medium reservoir to the dosing chamber. By using several admission channels spaced apart from one another, it is possible to ensure a more homogenous supply of the dosing chamber with the liquid to be dispensed. During the dispensing operation, local liquid deficits, which could lead to a reduced efficiency of the microdosing device, are avoided. In this way, a smaller dimensioning and/or a simpler design of the delivery means and thus a reduction in the production costs for the microdosing device can be achieved. A further advantage of having several admission channels lies in the fact that the energy requirement for dispensing a defined quantity of liquid can be reduced as a result of improved efficiency of the dosing chamber. In this way, an energy store provided for powering the vibration unit can be made smaller, thereby avoiding additional production costs. For efficient filling of the dosing chamber, the admission channels can be provided both with a uniform orientation on a single boundary surface of the dosing chamber and also with different orientations on one or more boundary surfaces of the dosing chamber. The vibration unit can be provided with one or more means for generating oscillations. These means are designed in particular as piezoelectric crystal oscillators. The means for generating oscillations cause an excitation of the boundary surface in one or more uniformly oriented or differently oriented oscillation directions acting in phase or out of phase.

In one embodiment of the invention, at least one storage chamber is connected to and communicates with the dosing chamber via at least one admission channel. A storage chamber is provided for temporary storage of liquid to be dispensed, in particular to make it possible to compensate for peak delivery quantities during the dispensing operation. In this way, the storage chamber also ensures further homogenization of the dispersion of the droplets and increased dosing accuracy. The storage chamber is for this purpose connected to and communicates with the dosing chamber via at least one admission channel, so that liquid stored in the storage chamber can flow directly into the dosing chamber via the admission channel. The storage chamber can be of a passive design, without its own delivery means, or of an active design, with its own delivery means. Filling of the storage chamber can take place only temporarily, in particular immediately before a dispensing operation, or can take place permanently.

In a further embodiment of the invention, the storage chamber is provided, at an end area directed away from the dosing chamber, with an equalization opening. By means of an equalization opening on the storage chamber, a pressure build-up in the storage chamber during filling with liquid is reduced or avoided. Moreover, the equalization opening makes it easier for the liquid to flow in the direction of the dosing chamber, because said equalization opening allows for pressure equalization in relation to an environment. In this way, the storage chamber has a low resistance for the liquid. A storage chamber can in particular be designed as a capillary, as a result of which particularly easy filling can be achieved through the capillary forces. Moreover, by using a capillary, it is possible in a simple manner to ensure complete filling and emptying without gas bubbles in the liquid, so that the stored liquid can be passed into the dosing chamber directly and in particular without measures for gas separation.

In a further embodiment of the invention, the equalization opening of the storage chamber is closed by a gas filter. By means of a gas filter, which can be designed in particular as a hydrophobic membrane filter, it is possible to prevent a situation where the liquid stored in the storage chamber is contaminated by microbes from an environment of the microdosing device. The gas filter is thus configured so that it allows only gas particles to pass through, while bacteria, viruses or liquid are prevented from passing through the gas filter. In this way, the gas filter can additionally be used as a means of limiting the filling of the storage chamber, since escape of the liquid from the storage chamber into the environment can be excluded. The filter can be arranged as a separate structural part on the storage chamber or, as in a preferred embodiment of the invention, can be incorporated as filter cartridge into the equalization opening of the storage chamber.

In a further embodiment of the invention, at least one admission channel is connected to a medium conveyor, and at least one connection capillary is provided between the medium conveyor and the storage chamber. A medium conveyor represents a communicating link between medium reservoir and dosing chamber and is for this purpose connected to at least one admission channel. In order to achieve advantageous dispersion of the liquid into the immediate environment of the dosing chamber, at least one connection capillary is provided between the medium conveyor and the storage chamber. The connection capillary can ensure direct supply of liquid to the storage chamber from the medium reservoir. Parallel supply to the storage chamber via the dosing chamber is also possible.

In a further embodiment of the invention, a medium branch formed by the connection capillary, storage chamber and gas filter has a lower flow resistance than the at least one dispensing opening. As has already been stated, the flow resistance of the dispensing opening is determined in particular by the size, geometry and material of the dispensing opening and the surface tension of the liquid. If a medium branch formed by the connection capillary, storage chamber and gas filter has a lower flow resistance than the dispensing opening, undesired escape of liquid through the dispensing opening during filling of the storage chamber via active delivery means can be prevented.

In a further embodiment of the invention, a measurement means is provided in the storage chamber for the purpose of determining the flow rate and/or the filling level. A measurement means can be designed, in particular, as a capacitive, inductive or optical flow meter or volume meter. With such a measurement means, it is possible in particular to ensure that a dispensing operation can be triggered only once the storage chamber is filled with a minimum level. The advantages of the storage chamber can be optimally exploited in this way. Determining a flowrate value using the measurement means in the storage chamber permits optimized adaptation of a delivery rate of the active delivery means and/or of the vibration unit so as to ensure an energy-efficient and homogeneous delivery quantity of the microdosing device. A flow of the liquid from the storage chamber can moreover be used as a direct or indirect measure for a quantity of liquid dispensed from the dosing chamber.

In a further embodiment of the invention, the storage chamber, at least in some sections, is provided together with the medium conveyor in one structural part. The structural part can be made in particular of silicon, plastic, metal or a composite. Production from plastic permits a particularly cost-effective design. In a particularly preferred embodiment, the storage chamber is embodied with medium conveyor, admission channels and at least one boundary surface of the dosing chamber in a single common structural part made of plastic.

In a further embodiment of the invention, a filling means is provided within the structural part, in particular a medium pump for conveying the liquid through the medium conveyor into the storage chamber and into the dosing chamber. A medium pump serves as active delivery means for transporting the liquid from the medium reservoir to the storage chamber and to the dosing chamber. By integrating the medium pump into the structural part in which the storage chamber and the dosing chamber and the medium conveyor can also be provided, it is possible to obtain a particularly compact and cost-effective structural group for a microdosing device. In a particularly preferred embodiment, the vibration unit, which is provided in any case for excitation of a boundary surface of the dosing chamber, can additionally be used as a means of driving the medium pump. This ensures extremely good energy efficiency of the microdosing device.

In a further embodiment of the invention, the admission channels are provided with different flow resistances. Depending on the design of the medium conveyor, storage chamber, dosing chamber and admission channels, different flow resistances can arise between the medium conveyor and the filling means and the individual admission channels opening into the dosing chamber. However, to ensure homogeneous supply of the dosing chamber from all the admission channels provided, their flow resistance can be adapted by geometric design and/or suitable arrangement on the dosing chamber or by special coatings, in such a way that a substantially identical flow resistance is obtained for all admission branches in relation to the medium conveyor and filling means.

BRIEF DESCRIPTION OF THE DRAWINGS

Further advantages and features of the invention will become evident from the claims and from the description of a preferred illustrative embodiment of the invention, set out with reference to the single FIGURE.

The single FIGURE shows, in a plane schematic representation, a microdosing device with dosing chamber and storage chamber.

DETAILED DESCRIPTION OF THE INVENTION

A microdosing device 1 has a dosing chamber which is designed as compression chamber 19 and which is delimited by boundary surfaces such as a membrane 2, a structural part 3 and a rear wall 4. Dispensing openings 9 designed as membrane pores 8 (not shown in detail) are provided in the membrane 2, and a liquid 10 contained at least temporarily in the compression chamber can be dispensed through these openings and into an environment of the microdosing device 1. Arranged on the rear wall 4 of the compression chamber 19 there is a vibration unit which is designed as an ultrasonic oscillator 5 and which can be powered at least temporarily, via control means (not shown in detail), with electrical energy in order to generate an oscillation. The compression chamber 19 is also provided with a number of admission channels, of which one is embodied as a direct inflow 6 and another as a reservoir inflow 7. While the direct inflow 6 is coupled directly to a filling means 16, the reservoir inflow 7 is supplied with liquid both from a connection capillary designed as channel 17 and also from a storage chamber designed as a meandering reservoir 11.

The reservoir 11 is incorporated as a meandering capillary structure in a structural part (not shown in detail) and has, at an end directed away from the reservoir inflow 7, an equalization opening designed as a vent 13. The vent 13 is closed off by a gas filter designed as a hydrophobic filter element 14, so that a barrier for microbes and liquid is present at the end of the reservoir 11. The channel 17 is connected to the direct inflow 6 and to the pump means 16. The pump means 16 is supplied with liquid, via a medium conveyor designed as a riser pipe 18, from a medium reservoir designed as a storage container 15. To determine a quantity of liquid dispensed from the microdosing device 1, a measurement means designed as a flow meter 12 is provided on the reservoir 11, said measurement means being provided with a control unit (not shown) for controlling the ultrasonic oscillator 5.

For a dispensing operation for precise dosing of a quantity of liquid into an environment of the microdosing device 1, it is initially provided that liquid is sucked from the storage container 15 via the riser pipe 18 by the pump means 16 and is delivered in the direction of the direct inflow 6 and the reservoir inflow 7.

Provided that the reservoir 11 at this point is not filled with liquid, the low flow resistance of the medium branch formed by the channel 17, the reservoir 11 and the filter element 14 generates a stream of liquid into the reservoir 11. The liquid does not pass through the membrane pores 8 into the environment, because the flow resistance of the membrane pores 8 is greater than the flow resistance of the medium branch. If the reservoir 11 and the compression chamber 19 are filled with liquid, the dispensing operation can be provided by activating the ultrasonic oscillator 5 via energy supply means and control means (not shown), so that, by oscillation of the rear wall 4 in the compression chamber 19, a pressure build-up takes place which leads to the flow resistance of the membrane pores 8 being overcome and thus to the liquid being dispensed into the environment.

Since, because of the oscillation of the ultrasonic oscillator, there is not a static pressure, but instead an oscillating pressure in the compression chamber 19, then, in phases of low pressure within the compression chamber, liquid can be actively delivered through the pump means 16 and/or can passively flow out of the reservoir 11 into the compression chamber. Therefore, during the entire dispensing operation, a uniform supply of liquid in the compression chamber is ensured, and, at the end of the dispensing operation, complete emptying of the reservoir 11 and of the compression chamber 19 can be provided.

The invention claimed is:

1. A microdosing device with a dosing chamber which at least temporarily receives a quantity of liquid and to which at least one dispensing opening is assigned, and with a vibration unit which is operatively connected to at least one boundary surface of the dosing chamber in order to cause this boundary surface to oscillate for the purpose of a dispensing operation, comprising at least two admission channels spaced apart from one another provided on the dosing chamber, wherein the microdosing device comprises a medium reservoir and wherein the microdosing device further comprises in addition to the medium reservoir at least one storage chamber for temporary storage of liquid to be dispensed, said storage chamber connected to and in communication with the dosing chamber via at least one admission channel and being designed as capillary, said storage chamber further comprising at an end area directed away from the dosing chamber an equalization opening open to an environment.

2. The microdosing device according to claim 1, wherein the equalization opening of the storage chamber is closed by a gas filter designed in particular as a hydrophobic membrane filter.

3. The microdosing device according to claim 1, wherein at least one admission channel is connected to a medium conveyor, and at least one connection capillary is provided between the medium conveyor and the storage chamber.

4. The microdosing device according to claim 3, further comprising a medium branch formed by the connection capillary, storage chamber and gas filter and having a lower flow resistance than the at least one dispensing opening.

5. The microdosing device according to claim 1, further comprising a measurement means provided in the storage chamber for the purpose of determining the flow rate and/or the filling level.

6. The microdosing device according to claim 3, wherein, at least in some sections, the storage chamber is provided together with the medium conveyor in one structural part.

7. The microdosing device according to claim 3, wherein, within the structural part, a filling means is provided for delivering the liquid through the medium conveyor into the storage chamber and the dosing chamber.

8. The microdosing device according to claim 1, wherein the admission channels are provided with different flow resistances.

* * * * *